(12) United States Patent
Lin et al.

(10) Patent No.: US 10,113,184 B2
(45) Date of Patent: Oct. 30, 2018

(54) MICROBE TRANSFORMANT FOR WEIGHT LOSS AND LIPID REDUCTION, THE METHOD FOR CONSTRUCTING THE TRANSFORMANT, AND APPLICATION THEREOF

(71) Applicant: NANJING SINOGEN BIOTECH & PHARMACEUTICAL INC., Nanjing (CN)

(72) Inventors: Yan Lin, Nanjing (CN); Rong Xiang, Nanjing (CN); Allan Zijian Zhao, Nanjing (CN); Fanghong Li, Nanjing (CN)

(73) Assignee: NANJING SINOGEN BIOTECH & PHARMACEUTICAL INC., Nanjing (CN)

( * ) Notice: Subject to any disclaimer, the term of this patent is extended or adjusted under 35 U.S.C. 154(b) by 0 days.

(21) Appl. No.: 15/560,948

(22) PCT Filed: Mar. 24, 2016

(86) PCT No.: PCT/CN2016/077184
§ 371 (c)(1),
(2) Date: Sep. 22, 2017

(87) PCT Pub. No.: WO2016/150392
PCT Pub. Date: Sep. 29, 2016

(65) Prior Publication Data
US 2018/0051303 A1    Feb. 22, 2018

(30) Foreign Application Priority Data

Mar. 26, 2015    (CN) .......................... 2015 1 0136916

(51) Int. Cl.
*A61K 49/00* (2006.01)
*C07H 21/04* (2006.01)
*A61K 48/00* (2006.01)
*C12N 15/90* (2006.01)
*A61K 38/27* (2006.01)
*A61K 8/64* (2006.01)
*A61Q 19/06* (2006.01)
*A61K 35/74* (2015.01)
*C07K 14/575* (2006.01)
*C12N 9/10* (2006.01)
*A61K 38/26* (2006.01)
*A61K 35/744* (2015.01)

(52) U.S. Cl.
CPC .............. *C12N 15/907* (2013.01); *A61K 8/64* (2013.01); *A61K 35/74* (2013.01); *A61K 35/744* (2013.01); *A61K 38/26* (2013.01); *A61K 38/27* (2013.01); *A61Q 19/06* (2013.01); *C07K 14/575* (2013.01); *C12N 9/1007* (2013.01); *C12N 15/902* (2013.01)

(58) Field of Classification Search
CPC ..... A61K 39/00; A61K 49/00; A61K 2039/52
USPC ...... 424/9.1, 9.2, 93.1, 93.2, 93.4; 536/23.1, 536/23.7
See application file for complete search history.

*Primary Examiner* — Rodney P Swartz
(74) *Attorney, Agent, or Firm* — CBM Patent Consulting, LLC (57) ABSTRACT

It discloses a transformant for weight loss and lipid reduction, which is obtained by recombining and substituting human oxyntomodulin gene into thymidylate synthase gene of *L.lactis* genome. Wherein the recombinant substitution is homologous recombination by artificially synthesizing gene sequences, making the sequence flanking the human oxyntomodulin gene derived from the homologous sequences of thymidylate synthase gene in the *L.lactis* genome, then the gene fragments are electroporated into *L. lactis*, to carry out homologous recombination.

5 Claims, 7 Drawing Sheets
Specification includes a Sequence Listing.

SEQUENCE LISTING

<160> NUMBER OF SEQ ID NOS: 7

<210> SEQ ID NO 1
<211> LENGTH: 201

-continued

<212> TYPE: DNA
<213> ORGANISM: Homo sapiens

<400> SEQUENCE: 1
atgaaaaaaa agattatctc agctatttta atgtctacag tgatactttc tgctgcagcc    60
ccgttgtcag gtgtttatgc ttcacaacat tctcaaggaa catttacatc agattattca   120
aaatatttag attctcgtag agctcaagat tttgttcaat ggcttatgaa tacaaaacgt   180
aatagaaata atattgcata a                                             201

<210> SEQ ID NO 2
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 2
ggttttattg tttcattagt                                                20

<210> SEQ ID NO 3
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 3
gagataatct ttttttttcat                                               20

<210> SEQ ID NO 4
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 4
ggaataacat tgcctaatga                                                20

<210> SEQ ID NO 5
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 5
tttattatta gggaaagcaa                                                20

<210> SEQ ID NO 6
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 6
atgacttacg cagatcaagt                                                20

<210> SEQ ID NO 7
<211> LENGTH: 20
<212> TYPE: DNA
<213> ORGANISM: Artificial Sequence
<220> FEATURE:

```
<223> OTHER INFORMATION: The sequence is synthesized

<400> SEQUENCE: 7
ttaaattgct aaatcaaatt                                              20
```

MICROBE TRANSFORMANT FOR WEIGHT LOSS AND LIPID REDUCTION, THE METHOD FOR CONSTRUCTING THE TRANSFORMANT, AND APPLICATION THEREOF

CROSS-REFERENCE TO RELATED APPLICATIONS

This application is the U.S. national phase of International Application No. number PCT/CN2016/077184 filed on 24 Mar. 2016 which designated the U.S. and claims priority to Chinese Application Nos. CN201510136916.4 filed on 26 Mar. 2015, the entire contents of each of which are hereby incorporated by reference.

STATEMENT REGARDING FEDERALLY SPONSORED RESEARCH OR DEVELOPMENT

Not Applicable.

THE NAMES OF THE PARTIES TO JOINT RESEARCH AGREEMENT

Not Applicable.

INCORPORATION-BY-REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

BACKGROUND OF THE INVENTION

1) Field of the Invention

The invention relates to the biological medicine field, in particular to a transformant for weight loss and blood lipid reduction, the construction method and use thereof.

2) Description of Related Art

Obesity is a health concern in the world today. In the Europe, USA and other developed countries, more than half of people overweigh, of which, 20-30% of them are obese patients. Obesity can not only affect people's quality of life, but also induce a series of diseases such as cardiovascular diseases, type 2 diabetes, and kidney diseases, etc., causing great harms to human health. Surveys have shown that the risk of hypertension is increased by 10% with every one-unit increase in BMI.

Although many factors such as genetics, endocrine disorders, diet structures, and lifestyle may contribute to obesity, the vast majority of obese patients are caused by unhealthy diet structures and life styles. At present, the treatments of obesity mainly include behavior therapy, drug therapy, and surgical treatment, etc. Behavior therapy, such as dieting and increasing exercises, cannot achieve good effect on weight loss. The body weight is easy to rebound and most people cannot achieve persistent long term weight loss. Surgical treatment may bring high risk, which is not easily accepted by majority of the patients. Therefore, most obese patients tend to receive drug therapy.

At present, the pharmaceutical drugs for weight loss include chemical medicines and Chinese herbal medicines. The chemical medicines generally act in central nervous system to suppress the appetite to achieve weight loss, such as Phentermine, Dexfenfluramine and Sibutramine, etc. However, these drugs could cause serotonin syndrome, with the side effect of mental state changes (such as anxiety, mania, and so on), or even cause hypertension and angina pectoris. Pancreatic lipase inhibitor orlista (orlistat, trade name Xenical) is chemical drug for weight loss, which can block the hydrolysis of triacylglycerol and inhibit fat absorption. But it has the adverse effects of steatorrhea, deficiency of lipid-soluble vitamins. The Chinese herbal medicines for weight loss are mainly plant extracts and dietary fibers, which can achieve weight loss through promoting bowel movement with dieting. Long-term use of herbal medicines may cause nutritional imbalance, water-electrolyte imbalance, fatigue, etc.

Oxyntomodulin (OXM) is a short peptide intestinal hormone secreted by intestinal epithelial L-cells. It is encoded by the proglucagon gene, which undergoes a variety of different processing to produce OXM, glicentin, glucagon-like peptide 1 (GLP-1), GLP-2 and other active peptide hormones. Human OXM contains 37 amino acids, with the effect of inhibiting food uptake and appetite, increasing fat mobilization. The OXM expression is closely related to the incidence of obesity. Obese patients have decreased secretion of OXM, while patients with anorexia (such as tropical diarrhea, jejunectomy) have increased secretion of OXM. OXM can regulate appetite and energy intake through three approaches: first, OXM directly acts on GLP-1 receptor of the gastrointestinal mucosa epithelial cell to inhibit the absorption of glucose and lipid; second, OXM acts on the vagus nerve to down-regulate the secretion of ghrelin and suppress the appetite. Studies have shown that subcutaneous OXM can reduce blood concentrations of ghrelin in rodents by 20%, while in human by 44%. Third, OXM stimulates the synthesis and secretion of thyroid hormone to increase the energy consumption and fat mobilization. Subcutaneous OXM can reduce food absorption and body weight of rodents, and reduce the fats. In the UK, 26 obese patients were enrolled in a double-blind trial. OXM was administered subcutaneously 30 minutes before meals for 4 weeks. The results showed that the body weights of patients in the treatment group were reduced by 2.3 kg, while those in the control group were reduced by 0.5 kg only, and the feeding habits and tastes of the subjects didn't change. The British Thiakis company chemically synthesized OXM-like peptides TKS1225 which has entered Phase III clinical trial. The U.S. Wyeth Pharmaceutical has purchased the exclusive right to use TKS1225. It is expected to develop TKS1225 into a new drug for weight-loss in recent years. However, TKS1225 and other OXM-like peptides are generally produced by chemical synthesis or bioengineering. The products are mostly powder and administered by injections, which have the shortcomings of high production costs, short in vivo half-life and inconvenience for medication. Thus, it is not easily accepted by patients with obesity.

The granted Chinese patent (200910041386.X) reported *Bifidobacterium* expressing human oxyntomodulin gene has achieved positive effect on weight loss and lipid reduction, but this *Bifidobacterium* expression system has a significant drawback. The plasmid vector pBBADs carries the ampicillin resistance gene that will introduce the ampicillin allergen into human body. If used for a long time, it may cause intestinal flora disorders and produce drug resistance of hosts. In this invention, the *L.lactis* strain does not contain an antibiotic resistance gene; it is a novel drug composition that will not introduce foreign allergens, with high degree of biological safety.

BRIEF SUMMARY OF INVENTION

One object of the present invention is to provide the transformant for weight loss and bloodlipid reduction; and the transformant has high expression of human oxyntomodulin without antibiotic resistance gene. Thus, it is safe to human and biosphere.

The second object of the invention is to provide a construction method of the transformant.

The third object of the invention is to provide the utilities of the transformant.

To solve the above technical problems, the invention adopts the following technical solutions.

A transformant for weight loss and blood lipid reduction, obtained by insertion into the *L.lactis* thyA (thymidylate synthase, thyA) gene with the codon-optimized human oxyntomodulin gene through homologous recombination.

Wherein, the human OXM gene, whose nucleic acid sequence can be optimized according to the preferred codons of the selected host, without changing the amino acid sequences, so that the human oxyntomodulin expression level can be increased in the transformant. Preferably, the nucleotide sequence is as shown in SEQ ID No: 1.

Wherein, the *L.lactis* is *L. lactis* NZ9000, *L. lactis* NZ3900 or *L. lactis* MG1363.

A method of constructing the transformant for weight loss and blood lipid reduction, comprising the following steps:

(1) Splice the upstream sequence of *L.lactis* thyA gene, the sequence codon-optimized human oxyntomodulin gene and the downstream sequence of *L.lactis* thyA gene successively and artificially synthesize the recombinant gene fragment;

(2) Electro-transform the newly constructed recombinant gene fragment into *L.lactis* for homologous recombination and select the thyA⁻ OXM⁺ strains.

In the invention, the thyA gene in the *L.lactis* genome is replaced by human OXM gene through homologous recombination, making constitutive-expression of human oxyntomodulin in *L.lactis*.

The uses of the transformant in preparing drugs and foods for weight loss and blood lipid reduction are within the scope of protection of the present invention. Wherein, the medicines are oral liquid, viable-bacteria powder, tablet or capsule oral medicines, and the foods are solid foods or beverages.

The uses of the transformant for weight loss and blood lipid reduction in preparing hypoglycemic agents in obese patients also are within the scope of protection of the present invention. Wherein, the medicines are oral liquid, viable-bacteria powder, tablet or oral capsule.

The uses of the transformant in preparing blood lipid reduction drugs for patients with fatty liver also are within the scope of protection of the present invention. Wherein, the medicines are oral liquid, viable-bacteria powder, tablet or oral capsule.

The invention has the following prominent features: the features of long-term growth and colonization of *L.lactis* in intestines, gene homologous recombination, the lactic acid bacteria with constitutive-expression of oxyntomodulin are screened and obtained. The goal is to attain the biological function of oxyntomodulin in regulating the appetite and energy absorption, weight loss and blood lipid reduction. This method does not require the separation and purification of oxyntomodulin polypeptide, with simple production process and low cost. It can be taken orally and convenient. Thus, this method overcomes the drawbacks of high production cost and medication inconvenience in production of oxyntomodulin-like peptides using genetic engineering or chemical synthesis.

The invention can achieve the following beneficial effects. Compared with the prior art, the invention has the following advantages.

1. The present invention constructs the recombinant *L.lactis* constitutive-expressing human OXM, which is a thymine-auxotroph strain. Since thymidine is an essential nutrient for the growth of *L.lactis*, thymidine is not available when thyA gene is deleted from genome. Therefore, the lactic acid bacteria after transformation cannot reproduce and grow in the external environment and produce any contamination on the environment or produce any effect on other microorganisms in the environment.

2. The strain constructed according to the present invention does not involve any element harmful to the human body and environment, including antibiotics, plasmids and genes which may produce toxic proteins; therefore, it can be used in the human body safely. The transgenic *Bifidobacterium* expressing OXM in Chinese Patent 200910041386 contains ampicillin resistance gene. A long-term use of this strain may induces drug resistance; moreover, after excreted in the feces outside the body, it may recombinants with other strains in the environment to produce "superbugs"; in addition, many people are allergic to ampicillin.

3. The bacteria have better effect on weight loss in obese mice than that of transgenic *Bifidobacterium* expressing OXM reported in the Chinese patent 200910041386.X. Within the same period of time and at the same doses, the *Bifidobacterium* can reduce the body weight by 21.4%, while the *L.lactis* can reduce the body weight by 31.1%, a significant increase. Moreover, the cholesterol levels in the blood and liver are reduced significantly, close to normal levels after treated with the OXM-expressing *L.lactis*. The animal experiments have shown that, after fed with OXM transgenic *L.lactis* for 1 month, the body weights of mice are reduced to normal level, and their fasting blood glucose levels also are close to normal.

4. The bacteria have the effect on weight loss and blood lipid reduction for diabetic mice. Its target populations will be extended to obese patients, diabetic patients and metabolic syndrome patients with lipid metabolism disorders.

DETAILED DESCRIPTION OF THE INVENTION

The present invention can be better understood from the following examples. However, it will be readily understood by those skilled in the art that the embodiments described are intended to be illustrative of the invention, not and should not be construed as limiting the invention as set forth in the claims.

Example 1: Preparation of OXM Gene Transformed L.lactis (1) Construction of Homologous Recombination Fragment:

According to the issued sequence of the genome of L. lactis, the sequence of 1000 bp upstream of the thyA gene start codon and 1000 bp downstream of the termination codon are found respectively.

The OXM nucleic acid sequences are optimized according to the human OXM amino acid and nucleic acid sequences, and with reference to codon usage frequencies of L.lactis. The resulting sequence is shown in SEQ ID NO: 1.

Chemical synthesis of gene fragment OXM-M: the sequence comprise of 1000 bp upstream of L.lactis thyA start codon, human OXM gene sequence, and 1000 bp downstream of L.lactis thyA gene termination codon.

(2) Preparation and Selection of Transgenic L.lactis Expressing OXM

Electro-transform human oxyntomodulin fragment OXM-M to the strain L.lactis NZ9000, named as L. lactis OXM.

Add 2 μl of OXM-M to 40 μl of L.lactis competent bacterial, mix well, place on the ice for 5 min, then transfer to a 0.4 cm electroporation cuvette.

Place the electroporation cuvette in the shocking chamber of the electroporation apparatus, and charge the capacitor. the condition was set to voltage 2000V, capacitance 25 μF, resistance 200Ω, and pulse length 4 msec.

After electroporation, remove the cuvette quickly, add to a 1 ml M17 culture medium, then place on ice for 5 min, and then incubate for 1 h at 30° C., then spread on a solid medium containing deoxythymidine and culture overnight. The next day, pick single colonies to inoculate them to the deoxythymidine-deficient and deoxythymidine-containing solid medium respectively; if strains grow in a deoxythymidine-containing solid medium but do not grow in a deoxythymidine-deficient solid medium, then the strains are positive bacteria.

(3). Genotyping of the Transformants Expressing OXM

Three pairs of PCR primers for genotyping are designed.

Primer 1: 1F (SEQ ID No: 2) 5'-GGTTTTATTGTTTCATTAGT-3', located at thyA upstream sequence;

1R (SEQ ID No: 3) 5'-GAGATAATCTTTTTTTTCAT-3', located at the beginning of the OXM gene sequence.

Primer 2: 2F (SEQ ID No: 4) 5'-GGAATAACATTGCCTAATGA-3', located at the end of the OXM gene sequence;

2R (SEQ ID No: 5) 5'-TTTATTATTAGGGAAAGCAA-3', located at thyA downstream sequence.

Primer 3: 3F (SEQ ID No 6) 5'-ATGACTTACGCAGATCAAGT-3', located at the beginning of the thyA gene sequence;

3R (SEQ ID No: 7) 5'-TTAAATTGCTAAATCAAATT-3', located at the end of the thyA gene sequence.

2 ul of bacterial cultures is used for standard PCR reaction.

Figure 1:
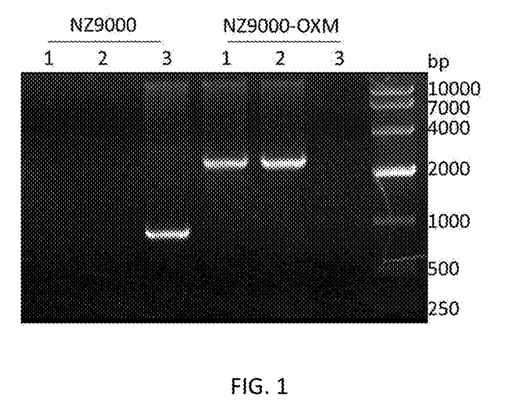
FIG. 1 shows the results of PCR genotyping.

PCR products are subjected to agarose gel electrophoresis. Results are shown in FIG. 1. The strain NZ9000 is not subjected to gene recombination, only the sequence of thyA is amplified by primer 3. Since the recombinant strain NZ9000-OXM lacks the thyA gene, there is no product for PCR amplified by primer 3, while fragments containing the OXM gene sequence are amplified by primer 1 and primer 2 respectively.

(4) Identification of OXM Expression

Inoculate 5 ml of culture medium and incubate overnight at 30° C.

On the next day, centrifuge the bacteria solution, add ⅓ volume of 100% trichloroacetic acid (TCA) to the supernatant and mix well, place on the ice for 20-30 minutes, centrifuge 10 min at 12000 rpm to precipitate the protein, then discard the supernatant; add 3 volumes (of the original sample volume) of acetone. Let the samples stand at room temp for about 10 min to allow the TCA to dissolve in the acetone, then centrifuge 10 min at 12000 rpm to precipitate the protein, then discard the supernatant; add 1×SDS loading buffer to dissolve the protein. Add lysozyme to the bacteria pellets, incubate for 30 min at 37° C. Mix well and add 500 μl of RIPA lysis buffer for ultrasonic extraction on the ice, then centrifuge 10 min at 12000 rpm to discard the pellets, add 1×SDS loading buffer to dissolve the protein.

After boiled at 95° C. for 5 min, all samples are separated by 18% SDS-PAGE electrophoresis, then transferred to PVDF membrane at constant voltage under ice bath condition, after blocked with BSA at room temperature for 1 h, rinsed with TBST for 3×5 min, then incubated with the rabbit anti-OXM antibody (1:500) overnight at 4° C. Rinsed with TBST for 3 times, 5 min each time, HRP labeled anti-rabbit secondary antibody (1:5000) was added, incubated 1 h at room temperature, rinse with TBST for 3 times, 5 min each time, and then developed using the enhanced chemiluminescent (ECL).

Figure 2:
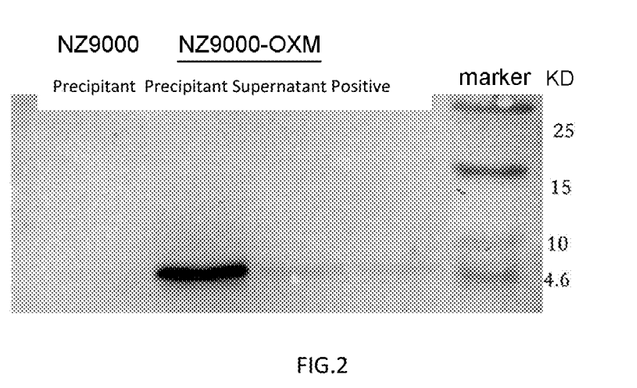
FIG. 2 shows immunoblotting analysis of OXM expression in *L.lactis*.

Results are shown in FIG. 2. The expression of OXM is not detected in L. lactis NZ9000 by immunoblotting, while the expressions of OXM are detected in the L.lactis NZ9000-OXM strain cells and the supernatant of culture medium, suggesting that the OXM is expressed in L.lactis NZ9000-OXM successfully and secreted extracellularly.

Example 2: Pharmacodynamics Experiments of OXM-Transformed Lactic Acid Bacteria to Weight Loss and Lipid Reduction (1) Prepare several weaned-stage B6 mice, and feed them high-fat diets until the obese mice models are constructed successfully. The Obesity criteria: (body weight of mice in the experimental group—average body weight of normal mice)/average body weight of normal mice >20%. Obese mice are divided into two groups, 10 mice in each group, and animals are fed high-fat diets continuously. One group is the control group, fed with L.lactis NZ9000; another group is the experiment group, fed with L.lactis NZ9000-OXM. At the same time, the normal control group is B6 mice fed normal diets without feeding with L.lactis.

Figure 3:
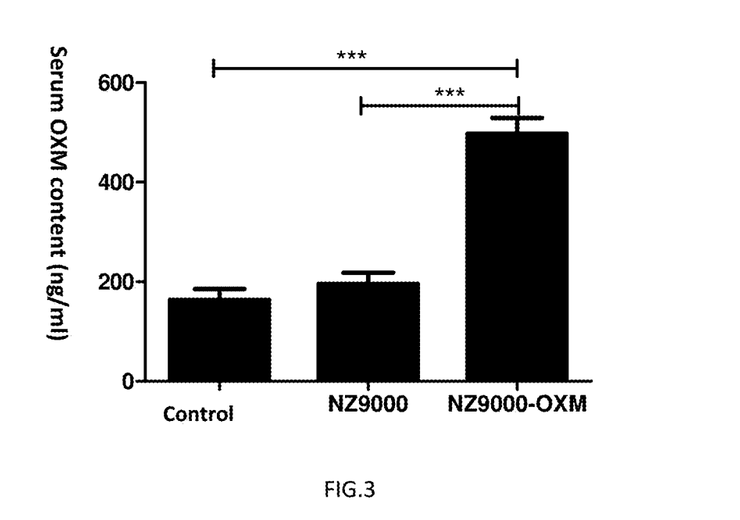
FIG. 3 shows the concentration of OXM in serum 5 hours after *L.lactis* feeding.
Figure 4:
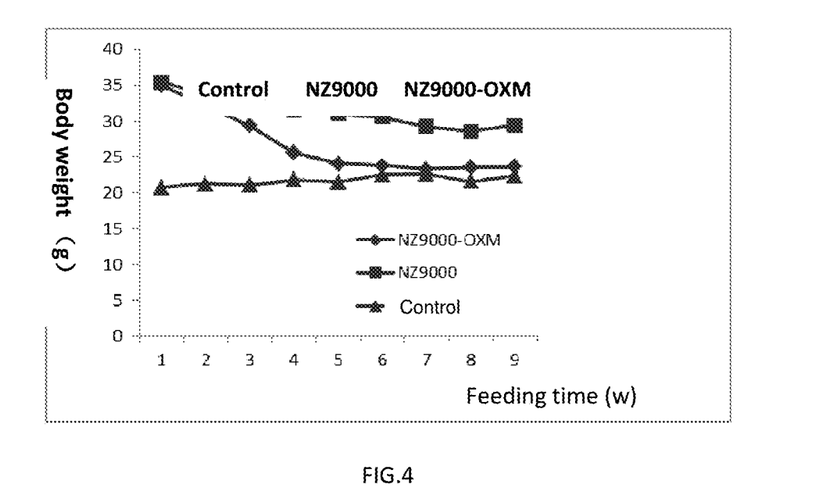
FIG. 4 shows the curve of body weight change after feeding obese mice with *L.lactis*.

(2) Each mouse is received 5×10⁹ CFU *L.lactis* by intragastric administration once every 2 days. The body weights, food intakes and other vital signs of mice are observed. Five hours after the first intragastric administration, the concentration of OXM in serum was detected by mass spectrometry. Results are shown in FIG. 3, after intragastric administration of NZ9000-OXM, the serum OXM content in mice was significantly increased nearly 2.5 times, about 497 ng/ml. The result further demonstrates that *L. lactis* NZ9000-OXM secrete and express OXM in mice. The comparative experiments show that, when feeding equal amount of OXM recombinant *Bifidobacterium* (patent No. 200910041386.X), the serum OXM concentration in mice is about 380 ng/ml, which is lower than that of OXM recombinant *L.lactis*. The body weight monitoring data are shown in FIG. 4. After obese mice are fed *L.lactis* NZ9000-OXM for 4 weeks, their body weights are significantly decreased. At the 5$^{th}$ week, their body weights are close to normal mice. Until the end of 9-week experiment, their body weight remains at about 24 g, while the body weight of mice fed with *L. lactis* NZ9000 is slightly reduced. Compared with the OXM recombinant *Bifidobacterium*, which has been granted patent right (200910041386.X), the *L.lactis* OXM can reduce the body weights of obese mice by 31.1%, while the OXM recombinant *Bifidobacterium* can reduce the body weight by 21.4% (FIG. 6) in equal time. Thus, *L. lactis* NZ9000-OXM achieves better weight loss.

Figure 5:
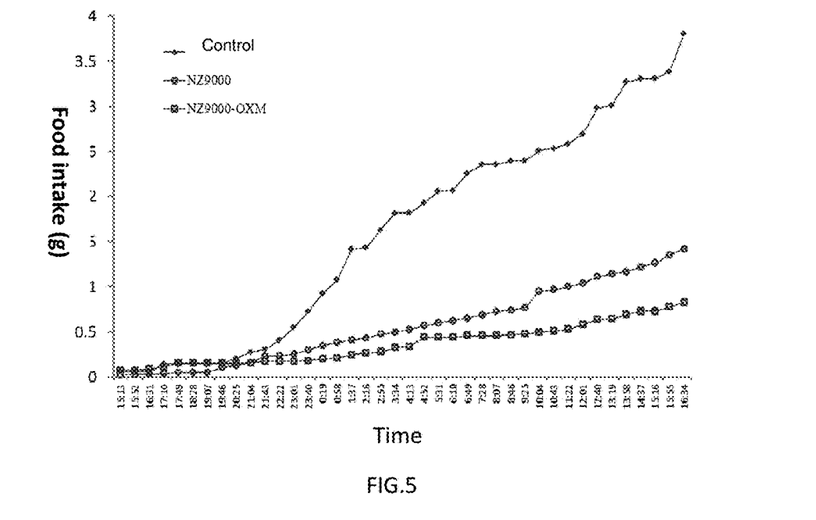
FIG. 5 shows the curve of food intakes 6 weeks after feeding obese mice with *L.lactis*.
Figure 6:
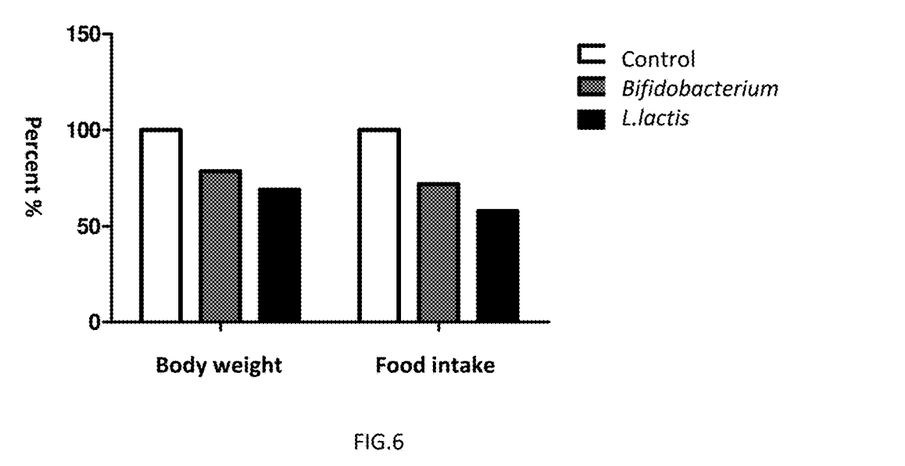
FIG. 6 shows the effect of *L.lactis* in comparison with *Bifidobacterium*.

(3) After 6 weeks of continuous feeding of *L.lactis*, the food intakes of mice are detected in metabolic cages for 24 h. Results were shown in FIG. 5. The food intakes of mice fed with *L.lactis* NZ9000-OXM are significantly reduced, about ½ of that in the *L.lactis* NZ9000 group. NZ3900-OXM decreases the food intakes of obese mice by 42.1% compared with the control group. Compared with the OXM transgenic *Bifidobacterium* reported in Chinese patent 200910041386.X, the OXM transgenic *Bifidobacterium* can decreases the food intakes of mice by 28.2% compared with the control group (FIG. 6). Thus, *L.lactis* NZ9000-OXM can better control the body weight by suppressing appetite and reducing the food intakes.

Figure 7:
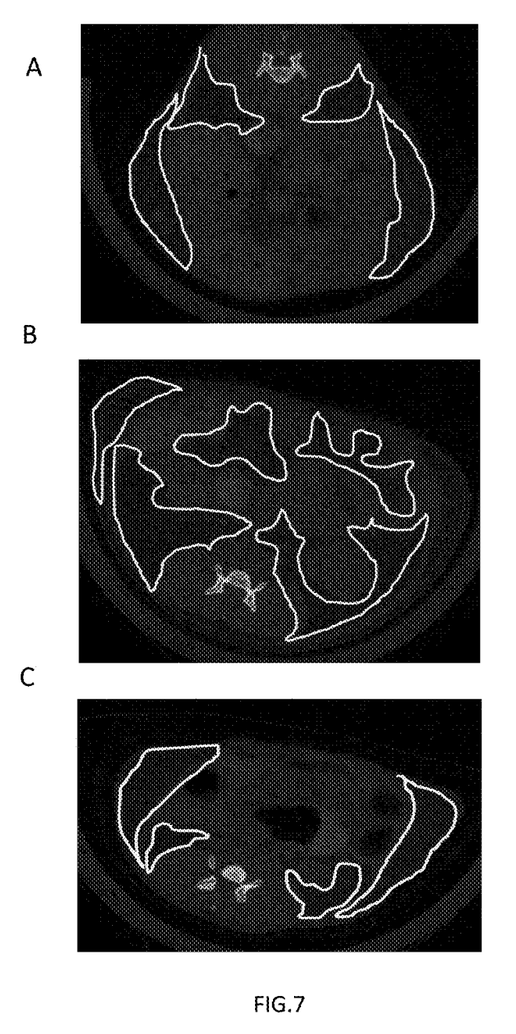
FIG. 7 shows the CT scanning of the abdomen after feeding obese mice with *L.lactis* for 6 weeks. A shows the normal mice; B shows obese mice fed with NZ9000; C shows obese mice fed with NZ9000-OXM (the light grey area within the white line represents the fat area).
Figure 8:
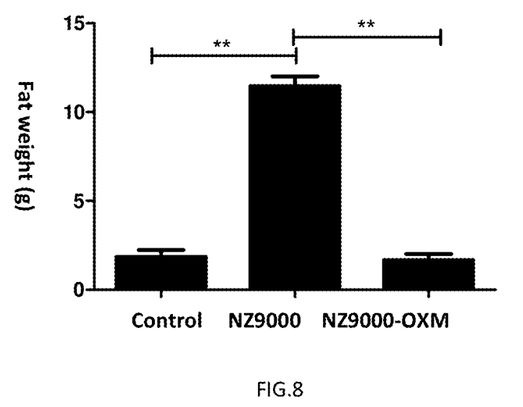
FIG. 8 shows the weight of body fats in obese mice after fed with L.lactis for 6 weeks.

(4) Six weeks after feeding of *L.lactis*, the distribution of the abdominal fat is measured with CT scanning. FIG. 7 is a cross-sectional scan of the abdominal cavity, and the light gray area delineated by white lines represents the adipose tissue. FIG. A represents the mice in the control group with normal diets. FIG. B represents the mice in the *L.lactis* NZ9000 feeding group, FIG. C represents the mice in the *L.lactis* NZ9000-OXM feeding group. It can be seen that the body fat content of mice in the NZ9000-OXM group is decreased significantly. The percentage of fats among the total body is calculated by CT analysis software and then fat weight for each mouse can be calculated. Data analysis is shown in FIG. 8. These results show that, the mice fed with *L.lactis* NZ9000 still have a large amount of abdominal fats, while the mice fed with *L.lactis* OXM have significantly less abdominal fat, and reduced to levels of normal mice, suggesting that *L.lactis* NZ9000-OXM has the effect of reducing body fat.

Figure 9:
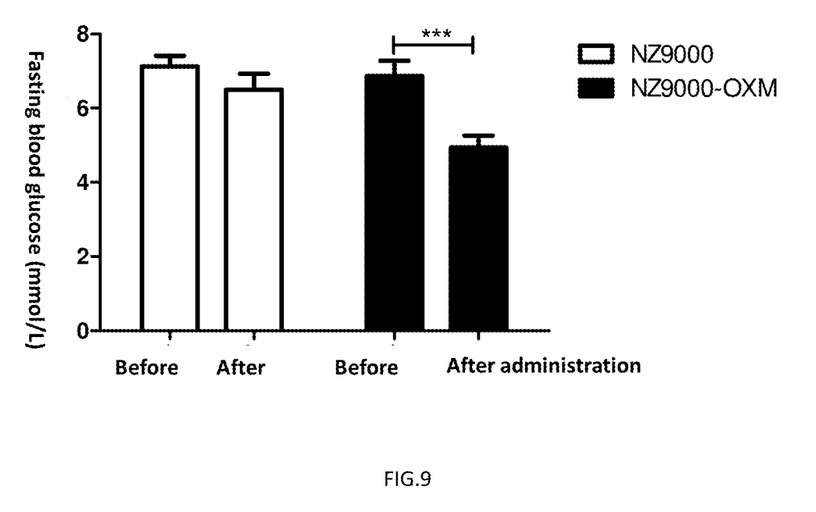
FIG. 9 shows the fasting blood glucose concentration in obese mice after fed with L.lactis for 6 weeks.

(5) After induction of obesity in mice with high fat diets, the fasting blood glucose increases to about 7 mmol/L (FIG. 9), which is significantly higher than that of normal mice. However, after 6 weeks of feeding *L.lactis*, the fasting blood glucose of mice in the *L. lactis* NZ9000 group is about 6.5 mmol/L. The fasting blood glucose level of mice in *L. lactis* OXM group returns to normal level of 5 mmol/L. Comparative experiments show that the OXM transgenic *Bifidobacterium* reported in Chinese patent 200910041386.X can not regulate fasting blood glucose in mice. Therefore, OXM recombinant *L.lactis* is superior to OXM recombinant bifidobacteria in reducing the fasting blood glucose.

Figure 10:
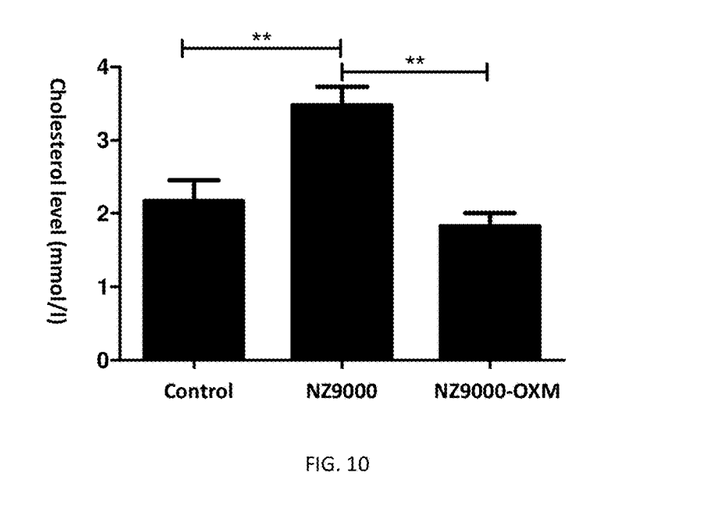
FIG. 10 shows the serum cholesterol level in obese mice fed with L.lactis for 6 weeks.

(6) After mice are induced obesity with high fat diets, their serum cholesterol level is 2.42 mol/l. At the end of the experiment, mice are sacrificed and serum cholesterol levels were measured. As shown in FIG. 10, the serum cholesterol level of normal mice is 2.167 mol/l, the serum cholesterol level of mice fed with *L. lactis* NZ9000 is 3.478 mol/l, and the serum cholesterol level of mice fed with *L. lactis* NZ9000-OXM is decreased to 1.83 mol/l, significantly lower than that of mice fed with *L. lactis* NZ9000. The OXM recombinant Bifidobacteria reported in the Chinese patent 200910041386.X can reduce the cholesterol level to approximately 2.4 mol/l in equal time. Thus, the *L. lactis* NZ9000-OXM provided in the invention can significantly reduce the serum cholesterol level.

Example 3: Pharmacodynamics Experiments of OXM-Transformed Lactic Acid Bacteria to Weight Loss and Lipid Reduction in Gene-Deficient Diabetic Mice 1. Prepare twenty 8-week db/db mice, divide them into two groups, 10 mice in each group. One group is the control group, fed with *L.lactis* NZ9000; another group is the experiment group, fed with *L.lactis* NZ9000-OXM. At the same time, the normal control group is B6 mice fed normal diets without feeding with *L.lactis*.

Figure 11:
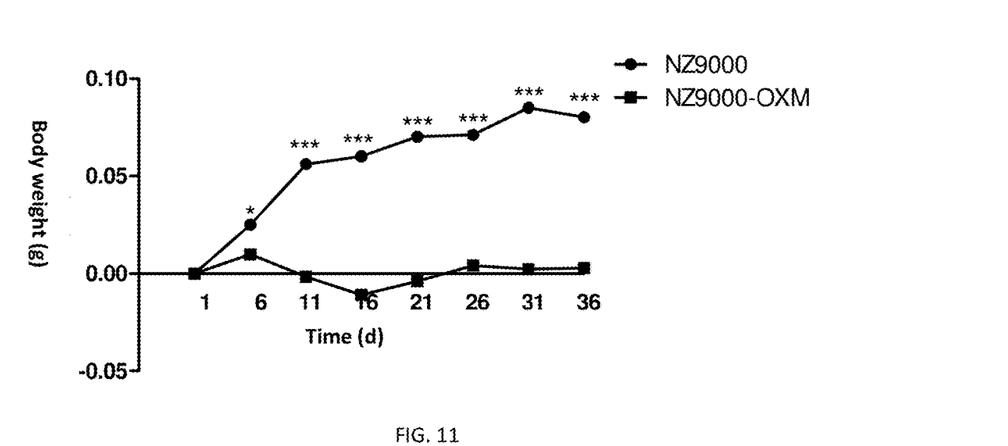
FIG. 11 shows the curve of body weight change in diabetic mice fed with L.lactis for 5 weeks.

2. Each mouse is received 5×10⁹ CFU *L.lactis* by intragastric administration every day. The body weight monitoring data are shown in FIG. 11. The body weights of mice fed with OXM can maintain unchanged compared with their own weight before administration. The body weights of mice in the NZ9000 group gradually increase, at the 5th week, increased by about 8%. The experiment shows that *L.lactis* NZ9000-OXM can effectively control the weight gain of diabetic mice.

Figure 12:
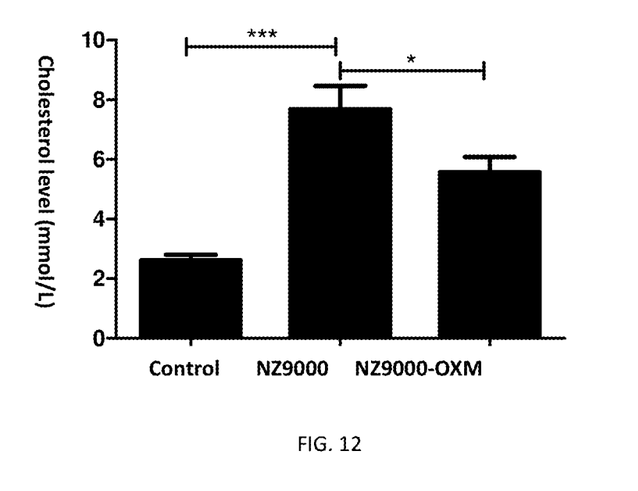
FIG. 12 shows the cholesterol level in serum of diabetic mice fed with L.lactis for 5 weeks.

3. At the same time, blood is drawn to detect the serum cholesterol levels (FIG. 12). The serum cholesterol levels in mice fed with OXM decrease significantly to 5.58 mol/l, significantly lower than that in the control group. This result suggests that *L. lactis* NZ9000-OXM can significantly reduce blood lipids in diabetic mice.

The present invention has shown that, OXM transformed lactic acid bacteria can express and secrete OXM in the intestinal tracts of mice, and the expressed OXM can suppresses appetite and inhibits energy absorption by acting on the corresponding receptors in the body, suggesting that OXM recombinant *L.lactis* has significant biological effects of weight loss, lipid reduction, and glucose reduction.

What is claimed is:

1. A transformant for weight loss and blood lipid reduction, wherein the transformant is obtained by replacing *Lactococcus lactis* (*L. lactis*) thyA gene with a codon-optimized human oxyntomodulin gene through homologous recombination.

2. The transformant for weight loss and blood lipid reduction according to claim 1, wherein the nucleotide sequence of the codon-optimized human oxyntomodulin gene has a DNA sequence shown in SEQ ID NO: 1.

3. The transformant for weight loss and blood lipid reduction according to claim 1, wherein the *L.lactis* is one strain of *L.lactis* selected from the group consisting of *L. lactis* NZ9000, *L. lactis* NZ3900 and *L. lactis* MG1363.

4. A method of constructing a transformant for weight loss and blood lipid reduction, comprising the following steps:

(1) ligate the upstream sequence of *L. lactis* thyA gene, the codon-optimized human oxyntomodulin gene and the downstream sequence of *L. lactis* thyA gene into a recombinant gene fragment;

(2) electro-transform the recombinant gene fragment obtained in step (1) into *L.lactis* for homologous recombination, to screen a thyA$^-$ OXM$^+$ bacteria resulting in the transformant.

5. A process for treating a human disease with the transformant of claim 1, comprising a step administering the transformant prepared as drug or food to a patient in need of treatment; wherein the human disease is obesity, diabetes or fatty liver.

* * * * *